United States Patent [19]

Takeda et al.

[11] Patent Number: 5,793,203

[45] Date of Patent: Aug. 11, 1998

[54] MEASUREMENT SYSTEM WITH NOISE REDUCTION CIRCUIT

[75] Inventors: Eriko Takeda, Tokyo; Toshikazu Nishino, Kawasaki; Masahiro Otaka; Ren Morinaka, both of Hitachi; Fuminobu Takahashi, Hitachinaka, all of Japan

[73] Assignee: Hitachi, Ltd., Tokyo, Japan

[21] Appl. No.: 567,278

[22] Filed: Dec. 5, 1995

[30] Foreign Application Priority Data

Dec. 5, 1994 [JP] Japan .................. 6-300532
Apr. 18, 1995 [JP] Japan .................. 7-092199

[51] Int. Cl.$^6$ .................. G01N 27/82; G01R 33/035; G21C 17/003
[52] U.S. Cl. .................. 324/219; 324/225; 324/226; 324/248; 324/262; 376/249; 505/162; 505/846
[58] Field of Search .................. 324/219, 220, 324/225, 226, 235, 240–243, 248, 262; 376/245, 249; 505/843, 845, 846, 162

[56] References Cited

U.S. PATENT DOCUMENTS

| | | | |
|---|---|---|---|
| 4,663,590 | 5/1987 | Gershenson et al. | 324/248 |
| 4,672,359 | 6/1987 | Silver | 324/248 X |
| 5,134,368 | 7/1992 | Otaka et al. | 324/248 X |
| 5,355,085 | 10/1994 | Igarashi et al. | 324/248 |
| 5,532,592 | 7/1996 | Colclough | 324/248 |

FOREIGN PATENT DOCUMENTS

| | | |
|---|---|---|
| 2319898 | 2/1977 | France . |
| 1-021379 | 1/1989 | Japan . |
| 64-21379 | 1/1989 | Japan . |
| 2-78983 | 3/1990 | Japan . |
| 5-126925 | 5/1993 | Japan . |
| WO-A-93/23750 | 11/1993 | WIPO . |

*Primary Examiner*—Gerard R. Strecker
*Attorney, Agent, or Firm*—Antonelli, Terry, Stout & Kraus, LLP

[57] ABSTRACT

A measurement system for measuring material deterioration in accordance with a magnetic field of the material in the presence of radiation. The measurement system includes a detection circuit which detects a magnetic field of the material and generates a signal indicative thereof which signal includes noise due to the radiation, a signal processing circuit including semiconductor devices to process the signal generated from the detection circuit and a noise reducing circuit for at least reducing noise in the generated signal which is due to the radiation. The signal processing circuit is installed at a place where a dose equivalent of radiation is equal to or smaller than that of a place where the detection circuit is installed.

54 Claims, 15 Drawing Sheets

MEASUREMENT SYSTEM WITH NOISE REDUCTION CIRCUIT

BACKGROUND OF THE INVENTION

The present invention relates to a measurement system for measuring material deterioration comprising a magnetic flux sensor using a superconductor, and particularly to a measurement system for measuring material deterioration which can be used even in the presence of radiation sources such as a nuclear reactor pressure receptacles and radiation emitted therefrom.

The most representative magnetic flux sensor using the superconductor in prior art is a SQUID (Superconducting Quantum Interference Device). The SQUID is a device capable of detection of the fine and weak magnetic field, using characteristics of the superconductor.

One of the applications of the SQUID in magnetic field detection is diagnosis of material deterioration. This is disclosed in Japanese Patent Laid-Open NO. 2-78983, etc.

FIG. 23 illustrates a configuration of the SQUID for detection of material deterioration according to the prior art. In the prior art, the SQUID 162 and detecting coil 163 are separately installed in different cryostats 164, and are connected by a flexible tube 165. Prior arts give consideration to placement of the SQUID 162 away from a radiation source, but special consideration has not yet been paid to the semiconductor circuit 161 used for signal amplification and signal processing in the presence of radiation.

Generally, the SQUID is a sensor to input an analog magnetic flux signal and to output an analog voltage signal, and the SQUID output is digitized to improve the functions of measurements by the SQUID, as is widely known. This is referred to as a digital SQUID. Similar to cases of many other sensor technologies, the digitization facilitates signal processing and data transmission (refer to FIG. 24); therefore, the digitization is not the technique inherent to the SQUID. Concrete methods are disclosed for example in Japanese Patent Laid-open NO. 64-21379 and Japanese Patent Laid-Open NO. 5-126925. However, no specific considerations have been given to the magnetometer using digital SQUID to be used in the presence of radiation sources or radiation emitted therefrom.

SUMMARY OF THE INVENTION

The following three points can be given as the major differences in measuring environment and accompanying phenomena thereof, as a result of comparison of the SQUID magnetometer utilized for measurement of material deterioration in the presence of radiation sources such as nuclear reactor pressure receptacles, and that used for biomagnetic measurement as representative application of the magnetometer using SQUID.

(1) Strong gamma ray is present even when the fuel rod is withdrawn out of the nuclear reactor pressure receptacle.

(2) The distance from the nuclear reactor pressure receptacle in which strong gamma ray exists and to the outer wall of the pressure receptacle is at least several meters.

(3) When the gamma ray in the nuclear reactor pressure receptacle passes through the SQUID, part of the energy is absorbed and produces quasi-particles, resulting in an increase of SQUID noise. Furthermore, since many magnetic substances are present in the pressure receptacle, environmental noise is larger than that of the biomagnetic measurement.

The following problems occur generally when the SQUID magnetometer of an analog operation type is used for these special environments, namely, when the drive circuit made of semiconductor elements is used, analog signals are output, and the SQUID magnetometer is controlled by the feedback by a FLL (Flux Locked Loop) circuit:

Firstly, such semiconductors as the bipolar transistor and MOS transistor are deteriorated due to effect of the gamma ray. When the amplifier is composed of semiconductors and installed close to the SQUID, as in the SQUID magnetometer according to prior arts, stability of measured results is reduced by deterioration of amplifier characteristic, and long-time measurement is impossible. Since the output signal itself from the SQUID is less stable, the FLL (flux locked loop) circuit has failed to perform stable operation. When the magnetometer using an analog SQUID is used in the prior art, there have been such problems as poor measurement accuracy and low reliability in measurement results.

In the case of a measurement using a digital SQUID, consideration has not been given to the placement of semiconductor circuit used for driving and signal processing. Generally, the magnetometer using the digital SQUID has an advantage that it is more resistant to external noise than the magnetometer using analog output SQUID. However, it is not yet recognized that noise is increased by radiation when it is used for the nuclear reactor pressure receptacle, and no countermeasures have been taken against this problem in the conventional magnetometer using digital SQUID. Namely, when the conventional magnetometer using SQUID is employed inside the nuclear reactor pressure receptacle, reduction in accuracy of measurement is occured as well.

The object of the present invention is to solve the problems of said prior arts, and to provide a measurement system for material deterioration which is capable of minimizing the deterioration of the signal processing circuit comprising at least a semiconductor, installing the detection circuit and signal processing circuit nearby, and detecting the position being measured; said system being capable of simultaneous measurement of a plurality of positions, ensuring an effective repair of a trouble in the event it has occurred, thereby providing a high degree of accuracy, reliability and efficiency as well as long-term continuous operation with stable circuit operation.

To achieve said objects, the present invention provides the following measurement system for measuring material deterioration:

(1) at least including a detection circuit comprising a magnetic flux sensor using superconductors at least in some parts, a signal processing circuit at least including a semiconductor to process the signal output from said detection circuit, and a signal transmitting means between said detection circuit and said signal processing circuit, wherein said signal processing circuit is installed at a place where the dose equivalent of radiation is equal to or smaller than that of the place where said detection circuit is located;

(2) at least comprising a circuit having greater enduring power to radiation and a circuit having weaker enduring power than said circuit, wherein said circuit having greater enduring power to radiation is used for measurement, whereas a circuit having weaker enduring power is used for signal processing;

(3) at least comprising a circuit having greater enduring power to radiation and a circuit having weaker enduring power than said circuit, wherein said circuit having greater enduring power to radiation is installed underwater;

(4) at least comprising a circuit having greater enduring power to radiation and a circuit having weaker enduring power than said circuit, wherein a substance to dampen radiation intensity is located between said circuit having greater enduring power to radiation and said circuit having weaker enduring power; or (5) at least including a detection circuit of analog signals and a circuit to process said analog signals, wherein said detection circuit of analog signals comprise substances which provide greater enduring power to radiation.

The measurement system for measuring material deterioration according to the present invention at least includes a detection circuit comprising a magnetic flux sensor using superconductors at least in some parts, a signal processing circuit at least including the semiconductor to process the signal output from said detection circuit, and a signal transmitting means between said detection circuit and said signal processing circuit, wherein said signal processing circuit is installed at a place where the dose equivalent of radiation is equal to or smaller than that of a place of said detection circuit.

The measurement system for measuring material deterioration according to the present invention does not place any restriction to radiation intensity at the position where the detection circuit comprising a magnetic flux sensor is installed. This will be explained with reference to the SQUID as a representative sensor using the superconductor. The SQUID comprises a superconducting ring to constitute inductance and Josephson junction device. The conductors of the superconducting ring and Josephson junction device are entirely made of metal, and inventors have found out that there is no deterioration of the element characteristics due to accumulation of electric charges caused by radiation such as gamma ray, unlike the case of a semiconductor circuit composed of the p-n junction and metal oxide semiconductor (MOS). This has made it clear that the characteristics of the magnetic flux sensor containing the superconductor are not deteriorated even when exposed to radiation. The present invention has been proposed based on this finding.

When the measurement system for measuring material deterioration is used to measure the deterioration of reactor structural material, it is necessary to install the detection circuit in the presence of very strong radiation such as in the place where the fuel rod is stored. However, the signal processing circuit including the semiconductor according to the present invention is installed at a place having radiation intensity equal to or smaller than the that of the place where the SQUID is installed; this makes it possible to prevent the semiconductor circuit characteristics from being deteriorated by irradiation, and to improve operation stability of the semiconductor and measuring accuracy, as well as to permit long-time measurement.

According to the present invention, in order to make the radiation intensity at the position of the semiconductor circuit lower than that at the SQUID position, a substance which dampens the radiation is placed between the SQUID and the semiconductor circuit, the distance between the SQUID and the semiconductor circuit is increased, or a combination of these measures is taken. Any of these three measures is capable of preventing deterioration of the semiconductor circuit. When the first two methods are compared, the installation of a radiation damping substance between the SQUID and the semiconductor circuit more effectively reduces the radiation intensity, if the radiation intensity at the position of the semiconductor circuit is kept the same, making it possible to reduce the distance between the SQUID and the semiconductor circuit. This provides accurate transmission of the output signal from the SQUID to the semiconductor circuit.

To ensure the underwater use of said measurement system for material deterioration, the low temperature vessel and the semiconductor circuit are provided with a means for waterproofing and means for resisting pressure, as well as a weight to prevent the vessel from floating. This is because the measurement system for measuring material deterioration uses water as a radiation damping substance. This design achieves the following advantages when said measurement system for measuring material deterioration is used inside the nuclear reactor pressure receptacle. In the first place, the water is normally present in the nuclear reactor pressure receptacle. Since said measurement system for measuring material deterioration permits underwater measurement, there is no need of removing water from the pressure receptacle. In the second place, water is liquid and capable of filling places having complicated forms, ensuring easy handling.

The measurement system for measuring material deterioration is provided with a means permitting underwater use, and is capable of diagnosing structural material for deterioration when water is present in the nuclear reactor pressure receptacle. Therefore, even when the signal detection circuit mainly including the semiconductor devices is installed on the pressure receptacle bottom or top, or between the outer walls of the shroud and the pressure receptacle, there is almost no deterioration in the characteristics of the signal detection circuit due to radiation, and said measurement system for measuring material deterioration provides highly accurate measurement and its long-time use. This will bring about the advantage that the signal processing circuit can be installed closer to the detection circuit than when it is placed outside the pressure receptacle, thereby making it possible to reduce the length of the wire connecting between the two circuits. This allows weak signals from the SQUID to be input into the semiconductor circuit with high accuracy, thereby improving the measuring accuracy of said measurement system for measuring material deterioration.

Furthermore, the measurement system for measuring material deterioration according to the present invention is installed in a place which has a lot of magnetic materials such as stainless steel of the nuclear reactor pressure receptacle. Since there is a very large environmental noise in the places where the measurement system is used, filters are provided to reduce or eliminate noise; the SQUID is equipped with superconducting shields and guard rings. This ensures accurate measurement of fine and weak signals even in the presence of loud environmental noise. Furthermore, the measurement system according to the present invention is provided with a means for eliminating noise resulting from irradiation, since the magnetic flux sensor in particular is subjected to exposure to radiation. The noise elimination means used herein should preferably be a low-pass filter having the cut-off frequency selected between 1 and 100 megaherz, because the frequency of the noise caused by gamma ray amounts to the order of several megahertz, but said cut-off frequency may be lower than that. Thus, this permits accurate transmission of output signals to the signal processing circuit even when the measurement system is exposed to radiation.

According to the present invention, the detection circuit and the low temperature vessel in which cryogen is placed is provided with a means for replenishing cryogen. This allows cryogen to be replenished, without having to remove the low temperature vessel out of the water, when they are placed under the water for measurement together with the low temperature vessel. This ensures an efficient, long-time continuous measurement. Furthermore, the low temperature vessel of the measurement system for material deterioration has a pressure adjusting means which keeps internal pressure constant. This prevents deterioration of measuring accuracy resulting from changes in the internal pressure.

In the measurement system for measuring material deterioration, the wire between the detection circuit and the signal processing circuit is longer than that of the magnetometer using the SQUID employed in the biomagnetic measurement; this results in larger external noise picked up by the wire. However, the signal from the SQUID is normally on the order of several microvolts, so measuring accuracy may be deteriorated if there is a larger external noise. To solve this problem, the measurement system for measuring material deterioration digitizes the output signal from the magnetic flux sensor or uses the amplifier to amplify the signal before it is transmitted to the signal processing circuit. In the case of digitization, said system utilizes the analog to digital converter based on the superconductive circuit thereby allowing the analog to digital converter to be placed adjacent to the magnetic flux sensor. Before the output from the magnetic flux sensor is deteriorated by induced noise, it is converted into digital signals on the order of millivolts, ensuring accurate signal transmission despite a long wire used to connect between the detection circuit and the signal processing circuit.

Furthermore, the measurement system for measuring material deterioration according to the present invention is provided with a means for detecting position. This ensures correspondence between the measuring positions and the measuring results in a spacious place such as the nuclear reactor pressure receptacle.

Moreover, said measurement system for measuring material deterioration according to the present invention uses screws or springs for connection between the signal detecting coil and the SQUID input coil constituting the magnetic flux sensor to hold them down, or both of them are manufactured on one and the same substrate and are integrated into one piece. The measurement system for measuring material deterioration has a standby circuit to provide means for coping with troubles in other places. When the first circuit has become faulty, it is switched to the standby circuit, thereby ensuring continued operation. Thus, this improves the reliability, and permits continued measurement by selecting the standby circuit in the event of troubles.

Furthermore, said measurement system for measuring material deterioration has a plurality of the magnetic flux sensors, allowing simultaneous inspection of many places, hence improved measuring efficiency.

When a high temperature superconductor is used as the magnetic flux sensor, the cryogen used for coolant is allowed to have liquid nitrogen temperature. This provides advantages of easier handling and lower cost than metal superconductors.

As discussed above, the configuration according to the present invention ensures a measurement system for measuring material deterioration ensuring; (1) reduction in deterioration of the signal processing circuit comprising at least the semiconductor, (2) installation of the detection circuit and signal processing circuit close to each other, (3) detection of measuring positions, (4) simultaneous measurement of many places, (5) effective measures to be taken in the event of a trouble, (6) long-term continuous operation with high accuracy, reliability and efficiency, and (7) excellent circuit operation stability.

As discussed in details, the present invention ensures;

(1) reduction in deterioration of the signal processing circuit comprising at least the semiconductor even in the presence of radiation sources and radiation emitted therefrom, (2) installation of the detection circuit and signal processing circuit close to each other, (3) detection of measuring positions, (4) simultaneous measurement of many places, (5) effective measures to be taken in the event of a trouble, (6) long-term continuous operation with high accuracy, reliability and efficiency, and (7) excellent circuit operation stability. Said measurement system for material deterioration having such effects will be described in details in the following Embodiments.

DESCRIPTION OF THE PREFERRED EMBODIMENTS

The following gives detailed description of the present invention with reference to embodiments:

First Embodiment

Figure 1:
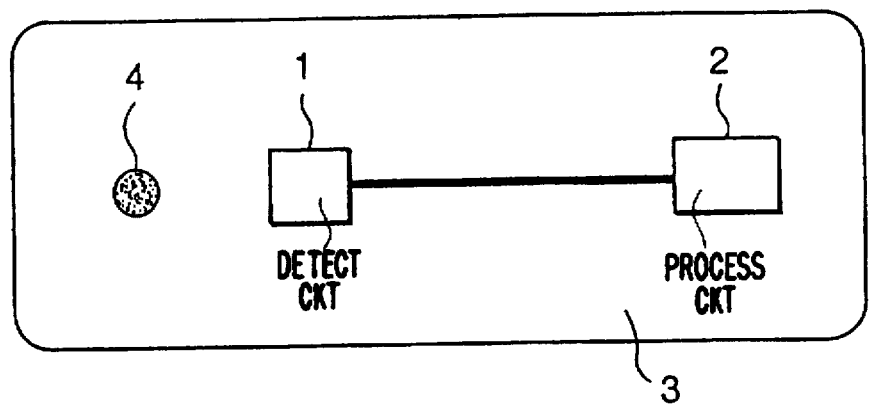
FIG. 1 is a block diagram illustrating an example of a first embodiment using water to shield radiation intensity.
Figure 2:
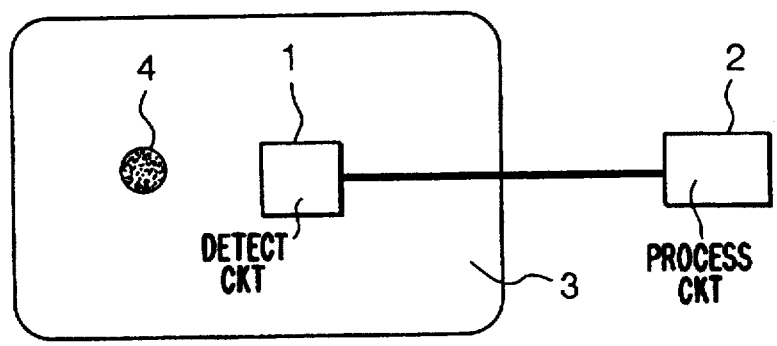
FIG. 2 is a block diagram illustrating another example in the first embodiment using water to shield radiation intensity.
Figure 3:
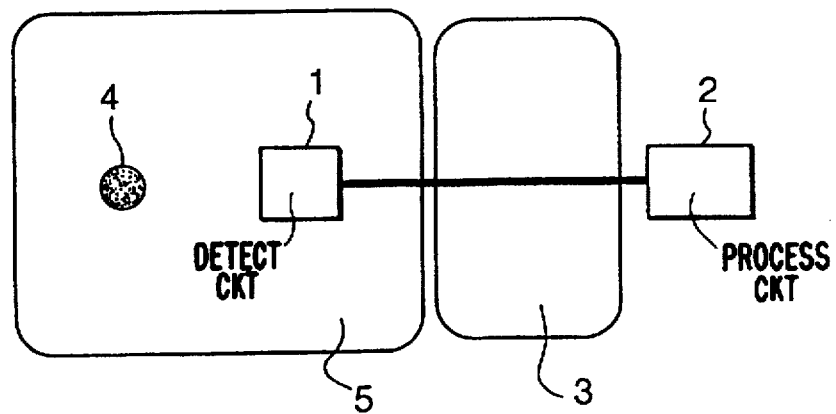
FIG. 3 is a block diagram illustrating still another example in the first embodiment using water to shield radiation intensity.

FIG. 1 illustrates the principle of the first embodiment according to the present invention. In the first embodiment according to the present invention, the detection circuit 1 and the signal processing circuit 2 are installed under water 3, and the signal processing circuit 2 is placed further from the radiation source 4 than the detection circuit 1, with water 3 being located between the two; thus, radiation intensity at the position of the signal processing circuit 2 is kept lower than that at the position of the detection circuit 1. This makes it possible to prolong the service life of the signal processing circuit 2, thereby ensuring stable operation of the measurement system for measuring material deterioration and improved reliability in measurements. In this embodiment, both the detection circuit 1 and the signal processing circuit 2 are placed under the water 3. As shown in FIG. 2, even when only the radiation source 4 and the detection circuit 1 are placed under water, radiation intensity is reduced by the water 3, giving the similar effect. As shown in FIG. 3, the same effect can also be gained by placing the water 3 between the area 5 where the radiation source 4 and the detection circuit 1 are present, and the signal processing circuit 2.

Figure 4:
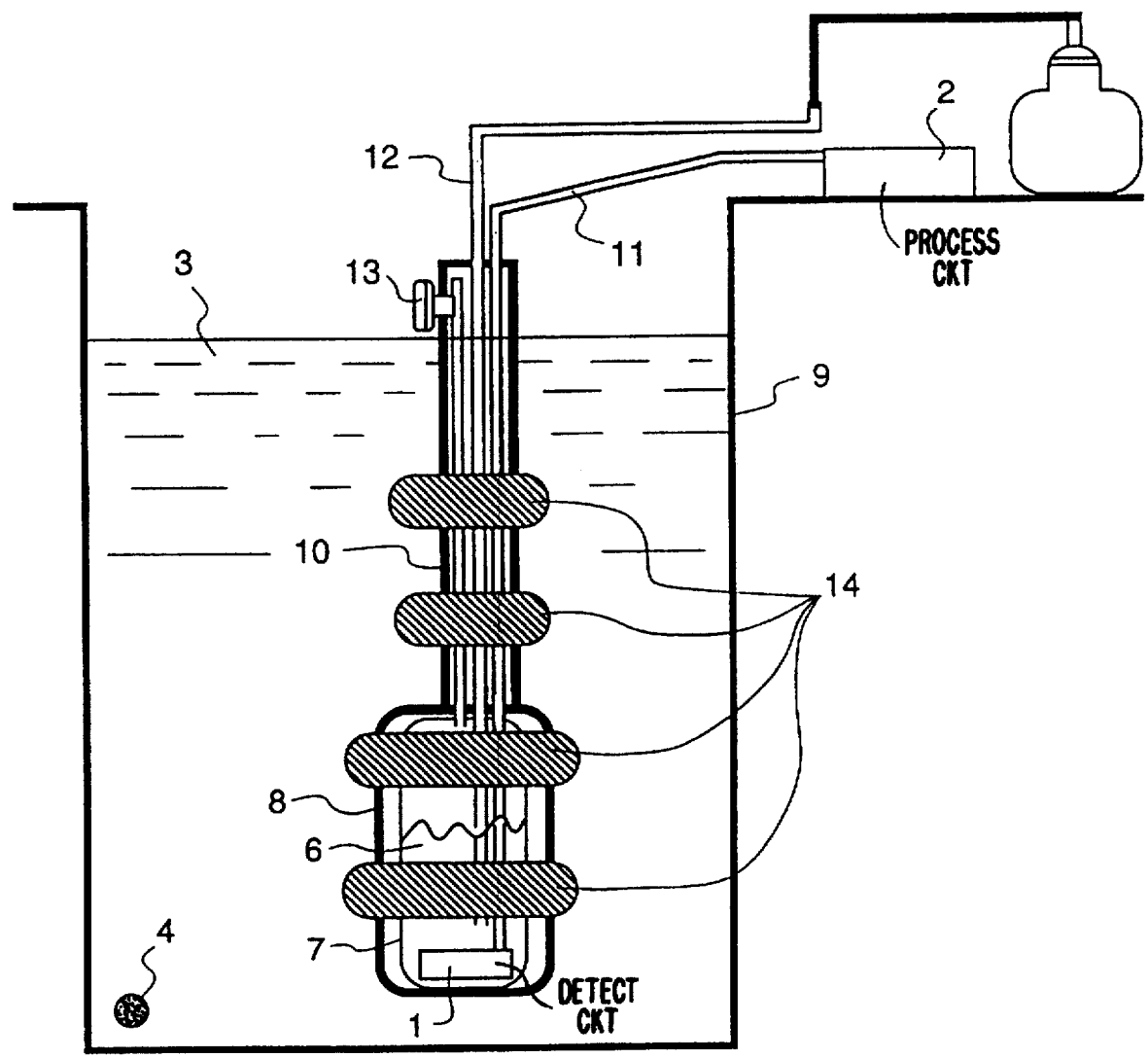
FIG. 4 is a drawing illustrating the measurement system for measuring material deterioration having its detection circuit placed underwater in the first embodiment.

The following describes the details of the embodiment with reference to FIG. 4 wherein the detection circuit 1 is used in the water 3: In this embodiment, the detection circuit 1 was installed inside the low temperature vessel 7 filled with the cryogen 6; then it was placed inside the pressure resistant vessel 8 provided with a means for waterproofing and means for resisting pressure, together with the low temperature vessel 7. The water 3 was supplied in a vessel 9 where the radiation source 4 was present, and the pressure resistant vessel 8 was installed therein. The signal processing circuit 2 was installed outside the vessel 9, and the pressure resistant vessel 8 was provided with a pipe 10 which was projected above the water level. The wire 11 to input signal from the detection circuit 1 into the signal processing circuit 2 was connected with the signal processing circuit 2 via the pipe 10. The low temperature vessel 7 and the pressure resistant vessel 8 were equipped with a cryogen supply pipe 12 to ensure that the cryogen 6 can be supplied into the low temperature vessel 7, as required. The low temperature vessel 7 and the pressure resistant vessel 8 were equipped with a pressure control valve 13 to ensure constant pressure inside the low temperature vessel 7. The pressure resistant vessel 8 and the pipe 10 were provided with a floatation preventing weight 14 to keep stable position even under water 3. This configuration provides a stable operation of the detection circuit 1 under constant pressure even under the water 3. This permits the cryogen 6 to be supplied whenever required; hence long-time continuous operation has become possible. The floatation preventing weight 14 allows the low temperature vessel 7 and the pressure resistant vessel 8 to be kept at the specified position even under the water 3, thereby preventing operation errors or reducing the accuracy caused by vibration of the system. This has succeeded in ensuring highly accuracy measurements.

The signal processing circuit 2 according to the present embodiment was installed outside the vessel 9. The signal processing circuit 2 can be provided with a means for waterproofing and means for resisting pressure and a floatation preventing weight to get the same effects. In addition, the distance between the detection circuit 1 and the signal processing circuit 2 can be reduced, making it possible to gain a compact system configuration, hence improved operability.

Figure 5:
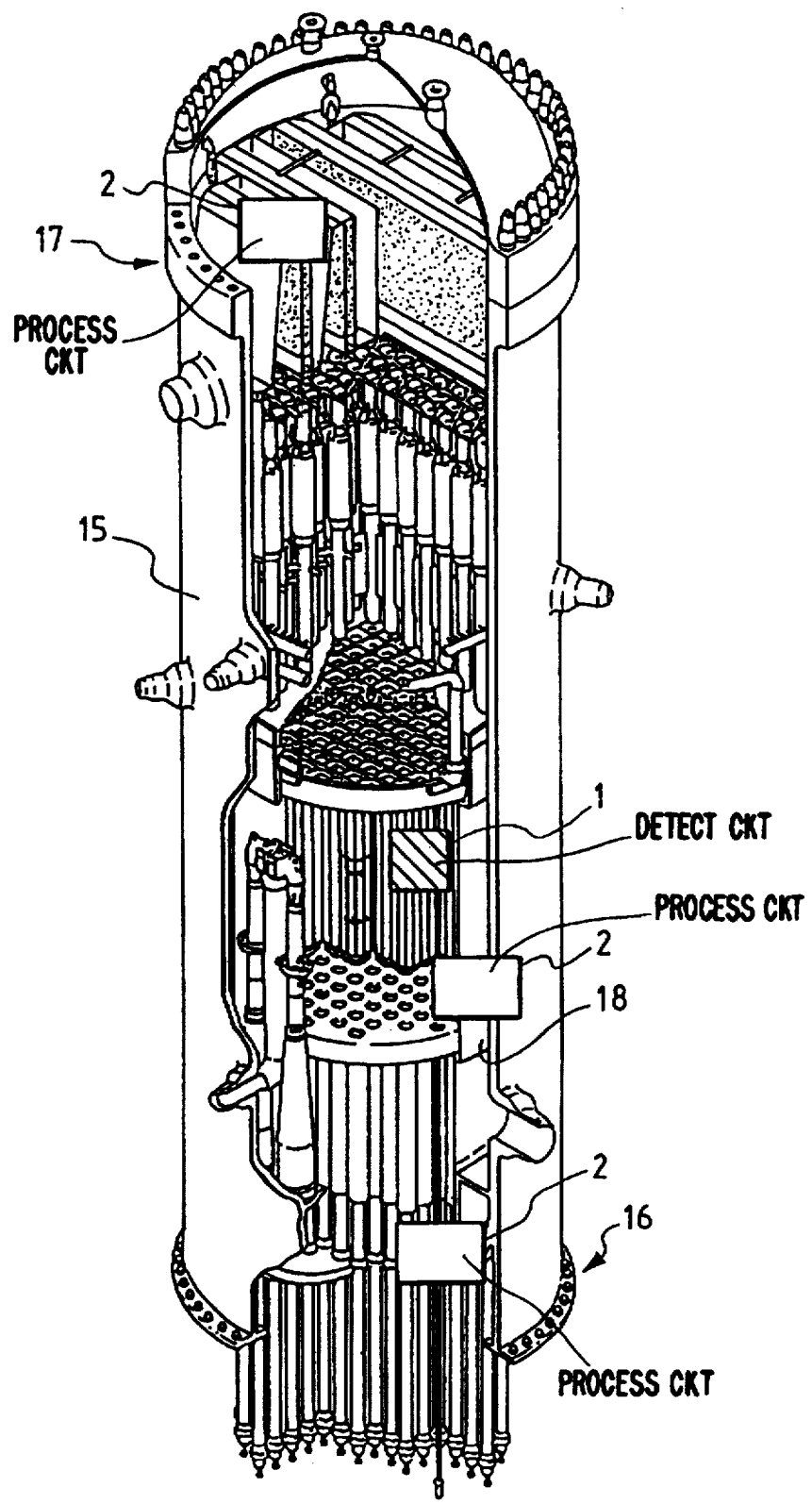
FIG. 5 is a drawing illustrating configuration of the signal processing circuit installed inside the nuclear reactor pressure receptacle in the first embodiment.

Use of the detection circuit 1 and the signal processing circuit 2 usable under water has made it possible to install the signal processing circuit 2 on the bottom 16 or top 17 of a pressure receptacle 15 as shown in FIG. 5, which is different from the pressure resistant vessel 8 as shown in FIG. 4, or in the area 18 between the shroud and the pressure receptacle, making a contribution to prolong service life of the signal processing circuit 2. In addition, the distance between the detection circuit 1 and the signal processing circuit 2 can be reduced, making it possible to ensure accurate transmission of signals of the detection circuit 1 to the signal processing circuit 2: this has lead to improved measuring accuracy.

Second Embodiment

Figure 6:
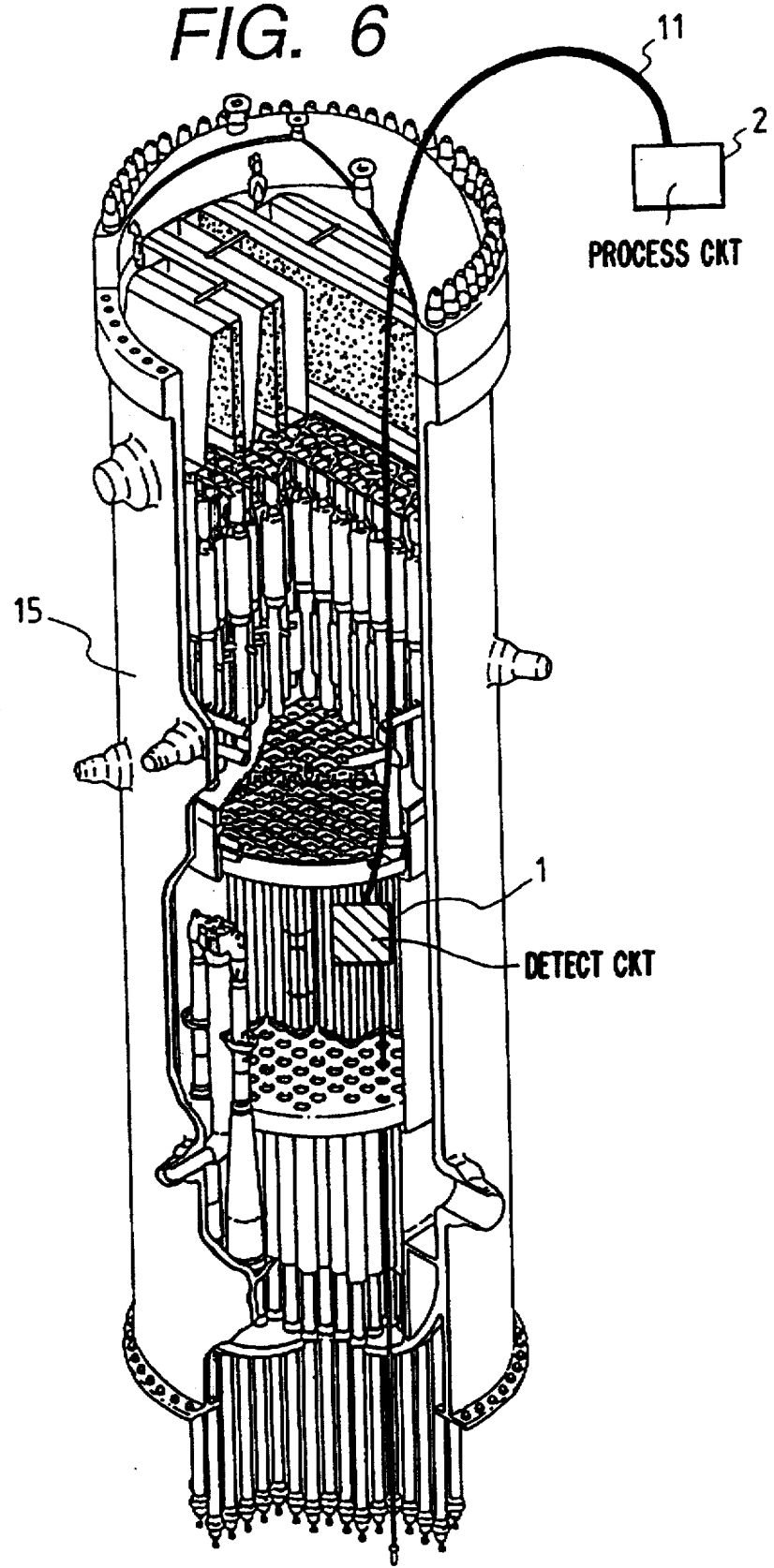
FIG. 6 is a drawing illustrating configuration of the signal processing circuit installed outside the nuclear reactor pressure receptacle in a second embodiment.
Figure 7:
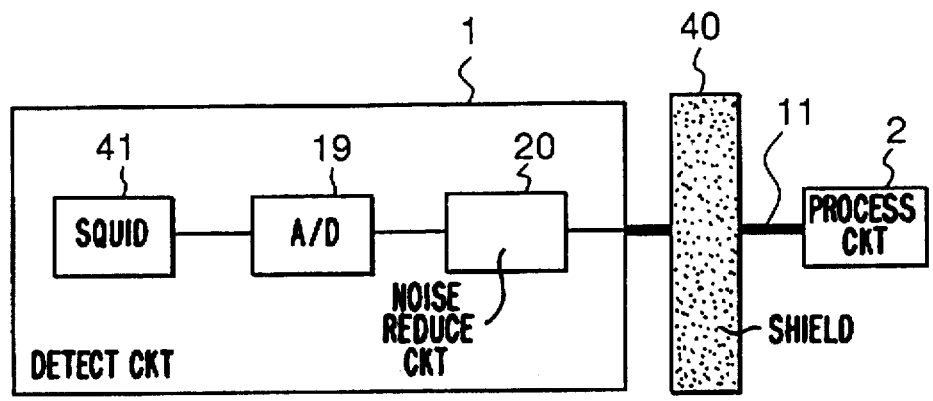
FIG. 7 is a block diagram illustrating the configuration using a digital SQUID in the second embodiment.

The embodiment 1 is mainly related to the case of using the water as radiation damping substance. The same effects can also be gained by using lead and concrete. This embodiment will be described with reference to FIG. 6. In the embodiment shown in FIG. 6, the signal processing circuit 2 is installed outside the pressure receptacle 15. In this case, the pressure receptacle 15 serves as a substance which reduces the radiation. Furthermore, installation of the signal processing circuit 2 away from the radiation source also makes radiation intensity at the position of the signal processing circuit 2 lower than that at the position of the detection circuit 1. Such a configuration prolongs the service life of the signal processing circuit 2, and provides a measurement system for material deterioration which ensures a long-term continuous operation with high accuracy and reliability. However, when the signal processing circuit 2 is installed outside the pressure receptacle 15 as in the present embodiment, the wire 11 connecting between the detection circuit 1 and the signal processing circuit 2 must be made longer. So the preferred circuit configuration must be as shown in FIG. 7. In the embodiment given in FIG. 7, the detection circuit 1 comprises a SQUID 41, an analog to digital converter 19 to digitalize the signal from the SQUID 41, and a noise eliminating means 20. Installation of a shield wall 40 between the detection circuit 1 and the signal processing circuit 2 has made radiation intensity at the position of the signal processing circuit 2 lower than that at the position of the detection circuit 1. The present embodiment digitalizes the output from the SQUID 41 by the analog to digital converter 19 to prevent deterioration of the signal resulting from the use of long wire 11 or external noise.

According to the embodiment shown in FIG. 7, the noise produced to the SQUID 41 by exposure to radiation is eliminated by the noise eliminating means 20. The noise eliminating means 20 given in the present embodiment is a low pass filter having a cut off frequency of 1 megaherz comprising the capacitor C and the resistor R. Furthermore, the analog to digital converter 19 is composed of a logic circuit using the Josephson junction device. In the analog to digital converter 19 shown in FIG. 7, the output voltage from the SQUID 41 is converted into current component by means of a resistor, and the current component is used to convert the analog signals into digital signals by assigning 0/1 signals to the information on whether or not the Josephson junction device should be switched. This configuration of the detection circuit 1 has ensured accurate transmission of the signal from the detection circuit 1 to the signal processing circuit 2, even when the wire 11 connecting between the detection circuit 1 and the signal processing circuit 2 is about 50 meters long. Thus, this configuration provides a measurement system for material deterioration featuring a long time use with high accuracy and a stable operation. Furthermore, it is clear that the same effects can be gained by the noise eliminating means 20 installed inside the signal processing circuit 2.

Figure 8:
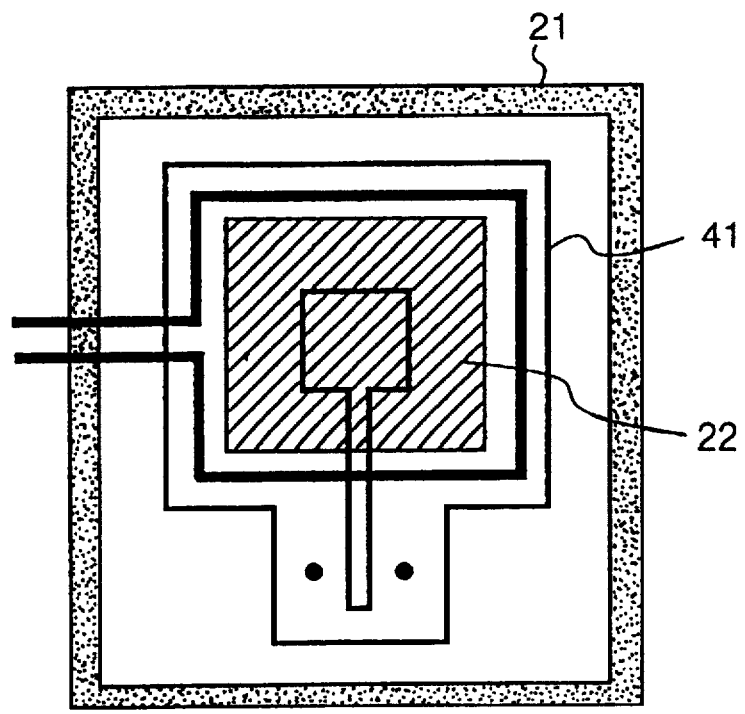
FIG. 8 is a drawing illustrating configuration of the SQUID provided with a noise eliminating means in the second embodiment.

The present embodiment has a low pass filter having a cut off frequency of 1 megaherz comprising the capacitor C and the resistor R as a means 20 to eliminate noise resulting from radiation. To eliminate other general noises, however, the SQUID 41 itself may be equipped with a superconducting shield 22 and guard ring 21, as shown in FIG. 8. This will reduce the frequency of magnetic flux trapping to the SQUID 41 due to vibration of surrounding magnetic materials, thereby providing a stable operation of the SQUID 41.

Third Embodiment

Figure 9:
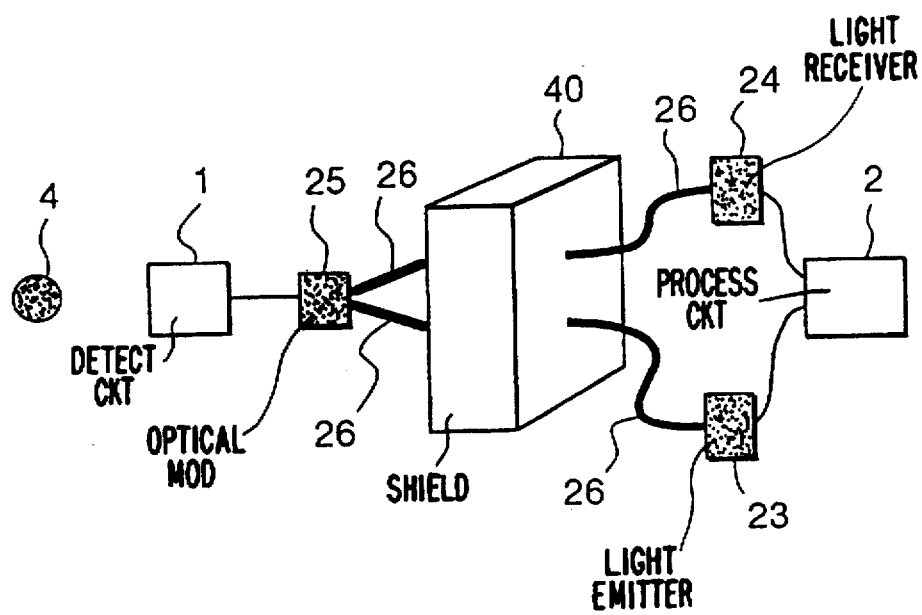
FIG. 9 is a schematic drawing illustrating the measurement system for measuring material deterioration using an optical means for signal transmission between the detection circuit and signal processing circuit in a third embodiment.

The following describes another embodiment with reference to FIG. 9. The embodiment given in FIG. 9 uses optical transmission of signals between the detection circuit 1 and the signal processing circuit 2. This embodiment comprises a light emitter 23, a light receiver 24, an optical modulation circuit 25 and an optical fiber 26, in addition to the detection circuit 1 and the signal processing circuit 2. In this embodiment, installation of a lead shield wall 40 between the detection circuit 1 and the signal processing circuit 2 has made radiation intensity at the position of the signal processing circuit 2 lower than that at the position of the detection circuit 1. Moreover, at least the light emitter 23 and the light receiver 24 should preferably be installed at a position with low radiation intensity. Optical transmission of signals between the detection circuit 1 and the signal processing circuit 2 prevents deterioration of signals resulting from induced current and external current, despite a long distance between the detection circuit 1 and the signal processing circuit 2, ensuring a highly accurate measurement system for material deterioration.

Fourth Embodiment

Figure 10:
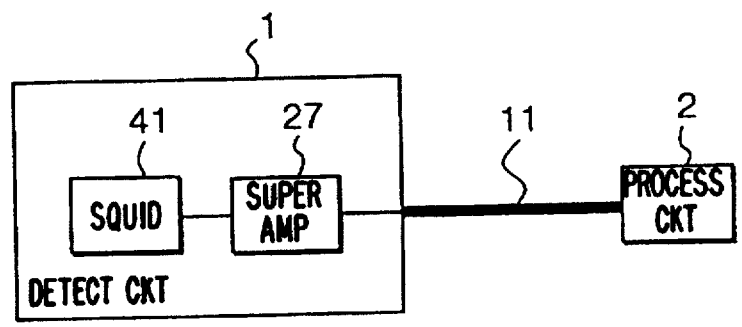
FIG. 10 is a schematic drawing illustrating the measurement system for measuring material deterioration in a fourth embodiment using the superconducting amplifier.

The following describes still another embodiment according to the present invention. FIG. 10 is a block drawing illustrating another embodiment of the present invention. According to the present invention, the output of the SQUID 41 is amplified to about 100 times by a superconducting amplifier 27 using the SQUID; then it is transmitted to the signal processing circuit 2. According to the present embodiment, the detection circuit 1 comprises the SQUID 41 and superconducting amplifier 27. The superconducting amplifier 27 is composed of a circuit with the SQUIDs arranged in 100 steps in series. In the case of the amplifier using the superconductor as in the present embodiment, there is deterioration of characteristics due to exposure to radiation, so it can be installed close the SQUID. Moreover, it has lower noise than superconducting amplifier in general, ensuring accurate amplification of the signal from the SQUID. Furthermore, in the case of the superconducting amplifier, it can be manufactured on the same chip as the SQUID. Use of the superconducting amplifier 27 equipped with the SQUID allows the output signal of the SQUID 41 to be amplified to the order of millivolts. Deterioration of the signal due to superimposition of the external noise can be reduced to below about 10 percent even when the wire 11 connecting it with the signal processing circuit 2 is long.

Accordingly, configuration of this embodiment amplifies the analog output of the SQUID 41 to provide accurate transmission even when the signal processing circuit 2 is installed outside the pressure receptacle, realizing a highly accurate measurement system for material deterioration. Furthermore, the input signal for the signal processing circuit 2 is analog signal, allowing feedback of the conventional flux locked loop circuit (FLL).

Fifth Embodiment

Figure 11:
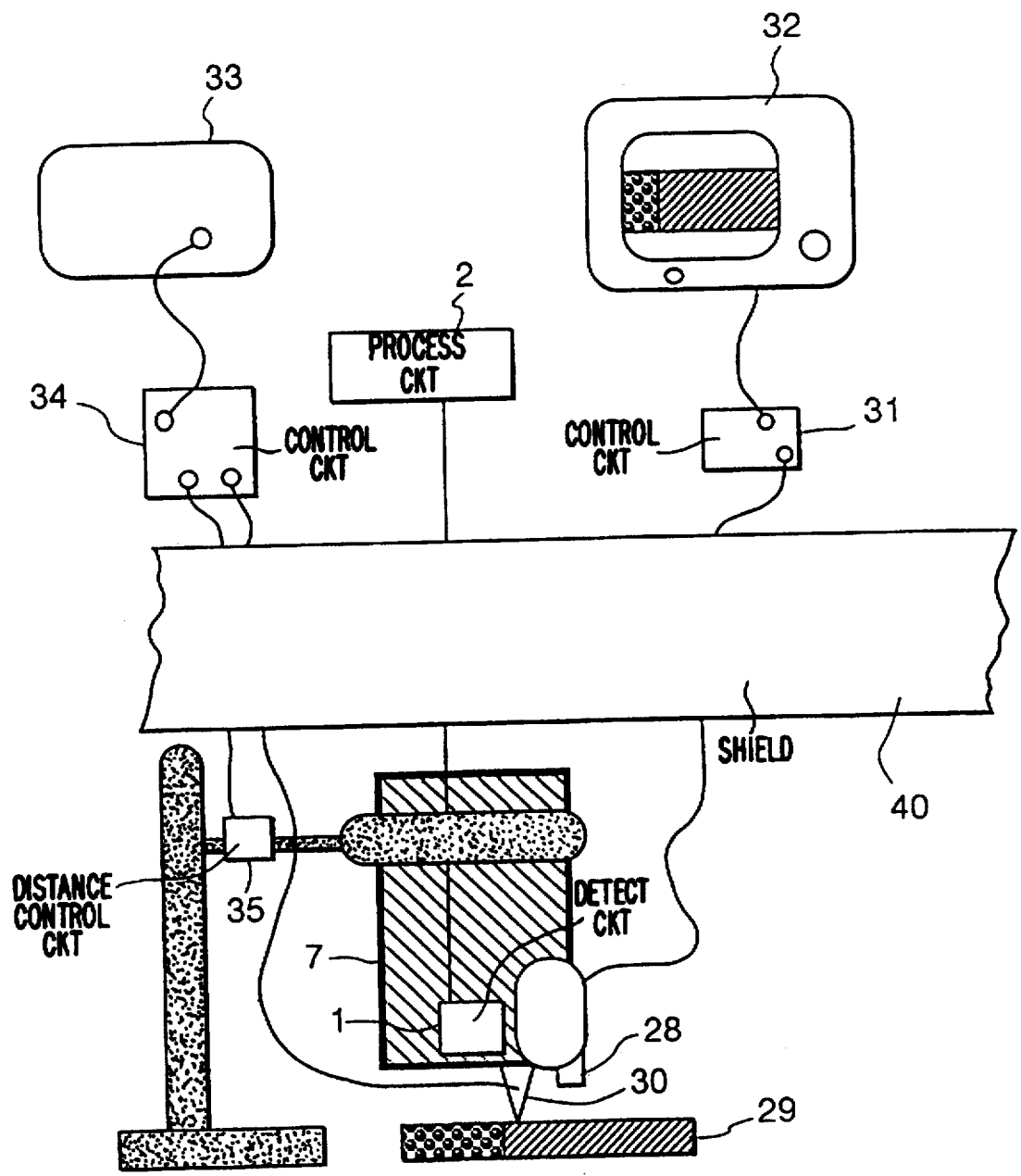
FIG. 11 is a schematic drawing illustrating the measurement system for measuring material deterioration in a fifth embodiment provided with a means for detecting positions.

The following describes a further embodiment according to the present invention. FIG. 11 gives a configuration of the embodiment according to the present invention equipped with a position detecting camera 28 to detect the measuring position. In the present embodiment a distance detector 30 is also installed to maintain a constant distance between the detection circuit 1 and the measured object 29. In the present embodiment, the position detecting camera 28 outside the low temperature vessel 7 is controlled by a control circuit 31, and the measuring position can be detected by observing the image from the position detecting camera 28 through a position detecting monitor 32. In the present embodiment, the distance detector 30 is mounted outside the low temperature vessel 7. The distance between the measured object 29 and the detection circuit 1 is kept constant through the control of a pressure detecting sensor 33, a control circuit 34 and a distance control circuit 35 so as to maintain the pressure at the tip position of the distance detector 30 always constant. This configuration allows the measuring point to be detected even in the remote operation mode. Since the distance between the measured object 29 and detected portion can be kept constant, accurate measuring results can be ensured even when there are undulations on the surface of the measured object 29. According to the present embodiment, the position detecting camera 28 is used as a means for detecting the position. Sound waves or probing method can also be used to detect the measuring position.

Sixth Embodiment

Figure 12:
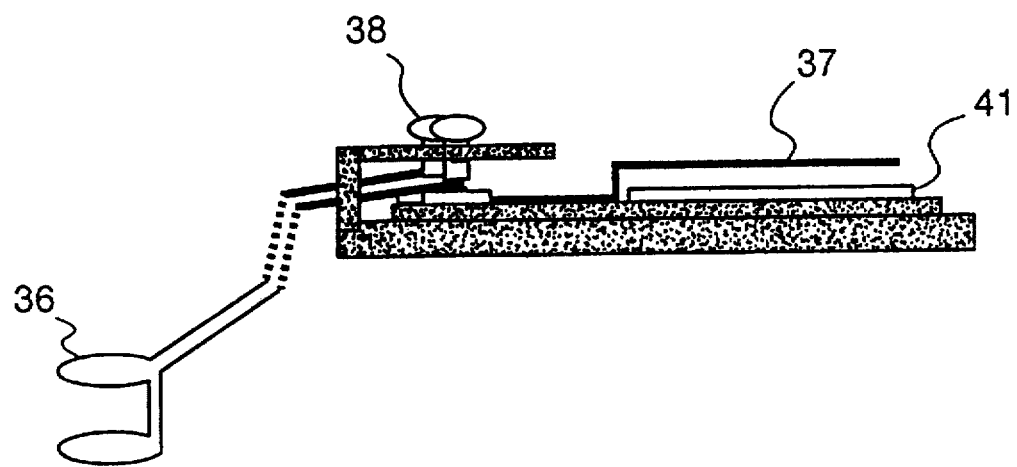
FIG. 12 is a schematic drawing illustrating the detection circuit in a sixth embodiment using screws for connection between the magnetic flux detecting coil and magnetic flux input coil.

The following describes a still further embodiment according to the present invention. In the present embodiment, the detection circuit 1 comprises the SQUID 41, a magnetic flux input coil 37 to the SQUID 41 and a magnetic flux detecting coil 36. In the present embodiment, the end of the magnetic flux detecting coil 36 and that of the magnetic flux input coil 37 are connected with each other by holding them down by screws 38, as shown in FIG. 12. Even when the measurement system for material deterioration is subjected to vibration, the deterioration at the connections can be reduced by using the screws 38 to hold down the connections between the magnetic flux detecting coil 36 and the magnetic flux input coil 37, compared with the case where they are connected by bonding wires. This ensures improved reliability of the measurement system for material deterioration. Furthermore, it is clear that the similar effects can be gained when the magnetic flux detecting coil 36 and the magnetic flux input coil 37 are connected by holding them with springs.

Figure 13:
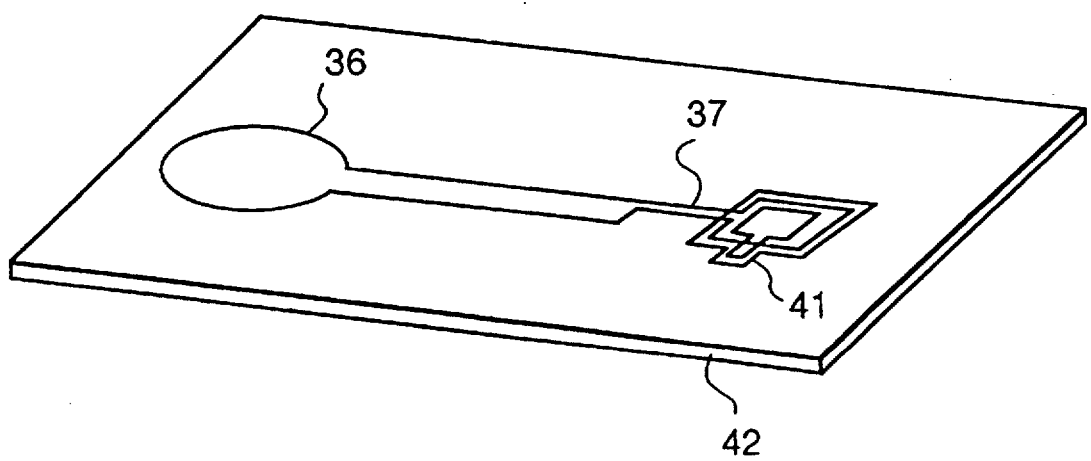
FIG. 13 is a schematic drawing illustrating the detection circuit in the sixth embodiment where the magnetic flux detecting coil and magnetic flux input coil are integrated into one piece.

As shown in FIG. 13, when the magnetic flux detecting coil 36 and the magnetic flux input coil 37 are manufactured on one and the same substrate 42 and are integrated into one piece without any connecting portion, it is possible to prevent separation of connections due to vibration which is likely to occur when they are linked by bonding wires, thereby ensuring greater reliability of the measurement system for material deterioration.

Seventh Embodiment

Figure 14:
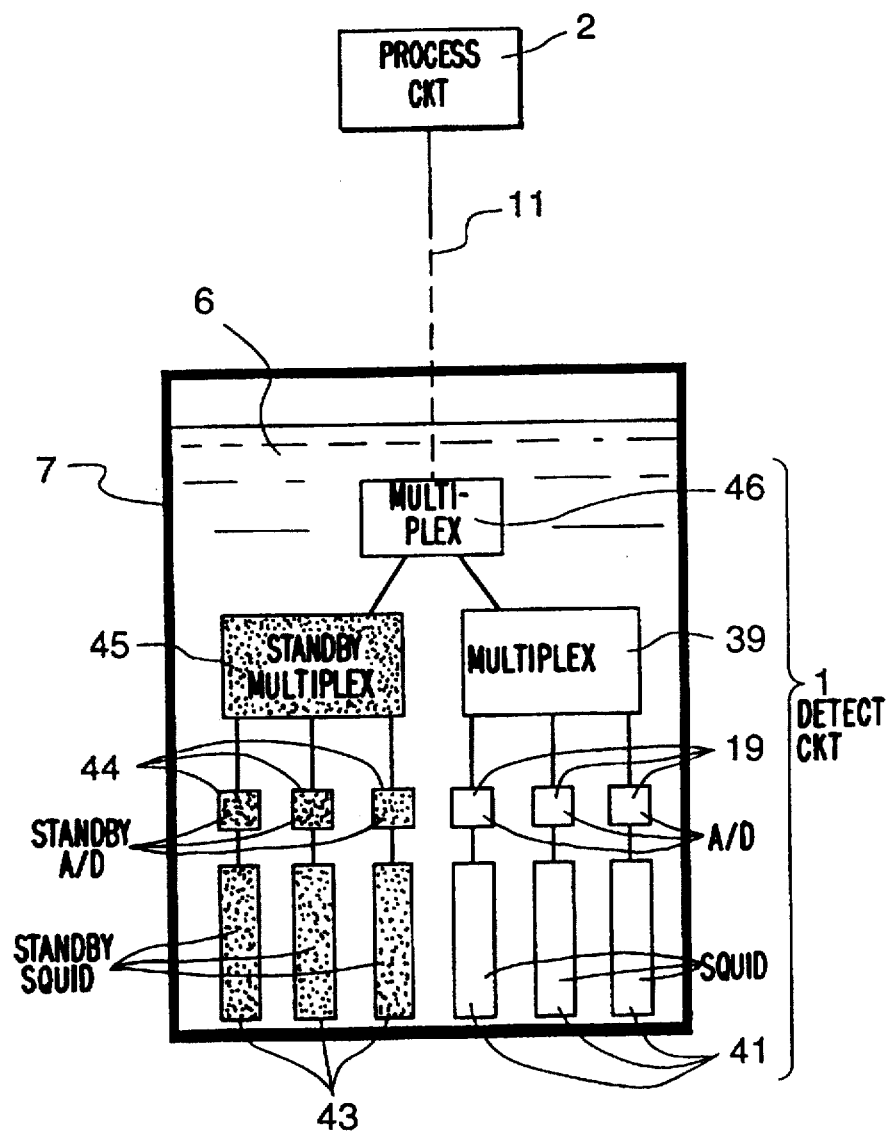
FIG. 14 is a schematic drawing illustrating the measurement system for measuring material deterioration in a seventh embodiment provided with a standby circuit and a plurality of channels.

The following describes another embodiment according to the present invention. In the present embodiment, the detection circuit 1 comprises a plurality of SQUIDs and multiplexers. The magnetic flux detecting coil and the magnetic flux input coil in the SQUID according to the present embodiment are integrated into one piece. In the present embodiment, the outputs of SQUIDs 41 are made digital by the analog to digital converters 19, as shown in FIG. 14, and these digital outputs are issued after having been switched by a multiplexer 39. Furthermore, to facilitate troubleshooting in the present embodiment, another set comprising a plurality of standby SQUIDs 43, standby analog to digital converters 44 to convert these outputs into digital signals, and a standby multiplexer 45 to emit these digital outputs by switching are provided in the low temperature vessel 7. In the present embodiment, another multiplexer 46 is installed on the next stage of the multiplexer 39 and the standby multiplexer 45. The multiplexer 46 switches the output from the multiplexer 39 and the standby multiplexer 45. The output from a set of the original circuit and output from the standby circuit are switched by the multiplexer on the later stage. When a plurality of the SQUIDs 41 are provided, as in the present embodiment, more than one position can be measured simultaneously, thereby ensuring reduced measuring time and improved efficiency.

Even when there are a plurality of the SQUIDs 41, use of the multiplexer 39 allows more than one output to be issued sequentially by switching, and makes it possible to reduce the number of wires 11. This will result in reduction of heat flow from the outside, thereby preventing cryogen 6 from evaporating and ensuring a long-time measurement. Furthermore, when the low temperature vessel 7 is immersed in water, installation of a standby circuit in the low temperature vessel 7, as in the present embodiment, will make it possible to select said standby circuit without having to draw water from the low temperature vessel 7, in the event that one of the circuits has failed; this is helpful in reducing the time loss by failure and increase in workloads. It is apparent that a standby circuit can be provided for the signal processing circuit 2, when the signal processing circuit 2 is immersed in water.

Eighth Embodiment

Figure 15:
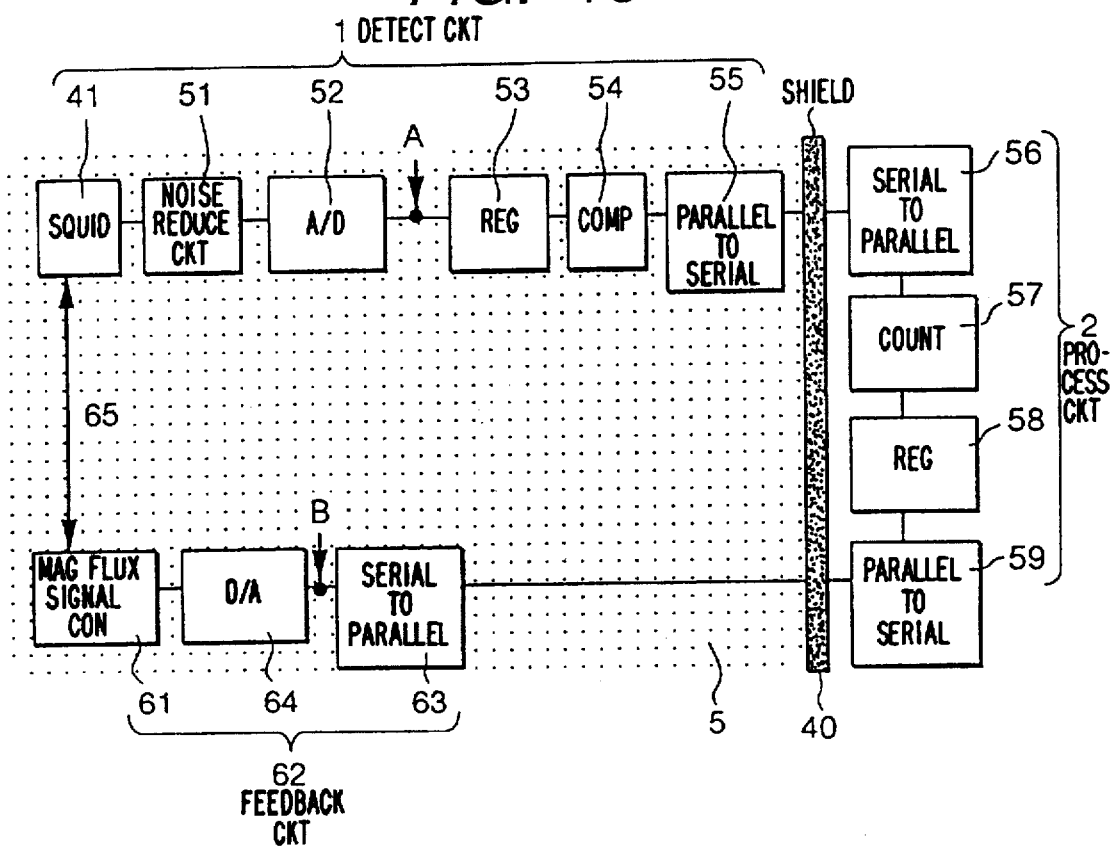
FIG. 15 is a block diagram illustrating the measurement system for measuring material deterioration in an eighth embodiment using the digital SQUID.

The following describes still another embodiment according to the present invention. FIG. 15 is a block diagram illustrating a circuit configuration in the embodiment. In the present embodiment, the detection circuit 1 comprises a SQUID 41, a noise eliminating means 51 to eliminate noise having occurred to the SQUID due to gamma ray, an analog to digital converter 52 to convert into a plurality of bits of the parallel digital signals the analog signals issued from the SQUID 41, a register 53 for temporary storage of the output from the analog to digital converter 52, a comparator 54 to compare the output from register 53 with a specified value, and a parallel to serial converter 55 to convert into the serial signals the parallel signals sent from the comparator 54. In the case of the circuit configuration shown in FIG. 15, the comparator 54 is included in the detection circuit 1, so only the result of comparing the output sent from the SQUID 41 with the value in the comparator 54 is transmitted to the signal processing circuit 2. This makes the amount of data to be transmitted smaller than when the comparator 54 is installed on the signal processing circuit 2.

Figure 16:
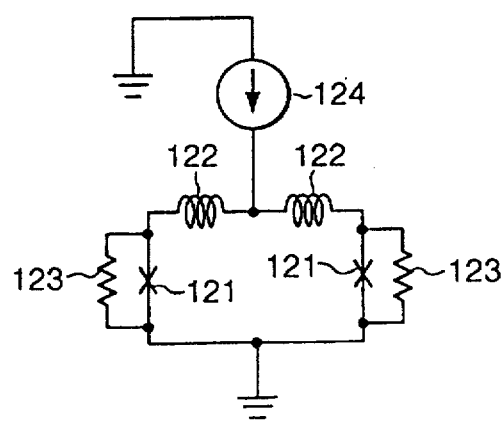
FIG. 16 is a circuit diagram of the SQUID in the eighth embodiment.
Figure 17:
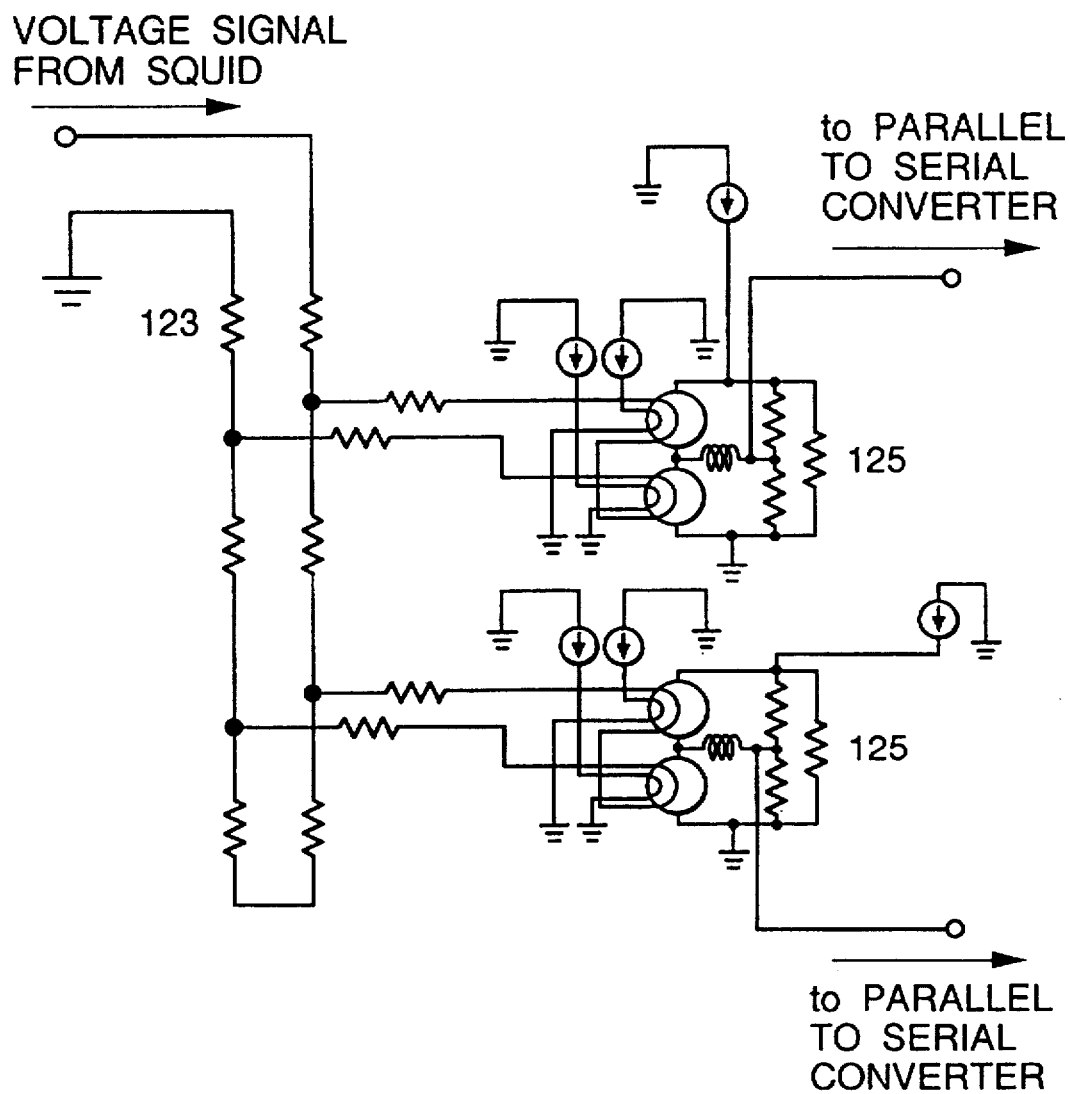
FIG. 17 is a circuit diagram of the analog to digital converter in the eighth embodiment.

As shown in the circuit diagram of FIG. 16, the SQUID 41 is a dcSQUID comprising two Josephson junction devices 121 and a superinductance 122. It has been manufactured by incorporating an Nb superconducting thin film and Josephson junction device 121 having a Nb/A10x/Nb structure. Reference numeral 124 denotes a DC power supply. The noise eliminating means 51 is a low pass filter having a cut off frequency of 1 megaherz comprising the capacitor C and the resistor R. As shown in FIG. 17, the analog to digital converter 52 is composed of a logic circuit 125 using the Josephson junction device 121.

At the analog to digital converter shown in FIG. 17, the output voltage is converted into current component by means of a resistor 123, and the current component is used to convert the analog signals into digital signals by assigning 0/1 signals to the information on whether or not the Josephson junction device should be switched.

As shown in FIG. 15, the signal processing circuit 2 comprises a serial to parallel converter 56 to convert the serial signal output from the detection circuit 1 into the parallel signal, a counter 57 to count the output from the serial to parallel converter 56, a resister 58 for temporary storage of the output from the counter 57, and a parallel to serial converter 59 to convert the parallel signal from the register 58 to the serial signal.

The feedback circuit 62 comprises a serial converter 63 to convert into the parallel signal the serial to parallel signal output from the signal processing circuit 2, a digital to analog converter 64 to convert into the analog signal the digital signal output from the serial to parallel converter 63, and a means 61 to convert into the magnetic flux signal the analog signal from the digital to analog converter 64. The magnetic flux signal produced by a means 61 to convert into the magnetic flux signal the analog signal from the digital to analog converter 64 is connected with the SQUID 41 by a magnetic flux coupling 65.

In the feedback circuit 62, the digital to analog converter 64 comprises a logic circuit using the Josephson junction device, and the means 61 to convert into the magnetic flux signal is composed of a resistor made by MoNx thin film and a superconducting inductance using a superconducting wire.

The detection circuit 1 and the feedback circuit 62 were disposed inside the nuclear reactor pressure receptacle in the presence of radiation source and radiation emitted therefrom. The signal processing circuit 2 was outside of the pressure receptacle 15 and the radiation shield wall 40 disposed outside of the pressure receptacle 15.

Noise occurs to the SQUID 41 contained in the detection circuit 1 due to radiation, and is eliminated by the noise eliminating means 51 in the present embodiment, without degradation in measuring accuracy. In the present embodiment, the noise eliminating means 51 is laid out between the SQUID 41 and the analog to digital converter 52; it is apparent that the same effects can be gained by placing it between the analog to digital converter 52 and the register 53 as indicated by point A in FIG. 15.

In the present embodiment, the detection circuit 1 and feedback circuit 62 placed inside the nuclear reactor pressure receptacle are connected to the signal processing circuit 2 installed outside the nuclear reactor pressure receptacle by a 10-meter-length wire. Accurate signal transmission is ensured because signal transmission is carried out after signals from the SQUID 41 have been converted into digital signals, and noise produced by gamma ray has been eliminated by the noise eliminating means 51.

Thus, said configuration of the present embodiment provides a measurement system for material deterioration featuring a long time use with high accuracy and a stable operation.

In addition, the resistor 58 disposed in the signal processing circuit 2 may be disposed at the position in the feed back circuit 62 shown in FIG. 15 as point B.

Ninth Embodiment

Figure 18:
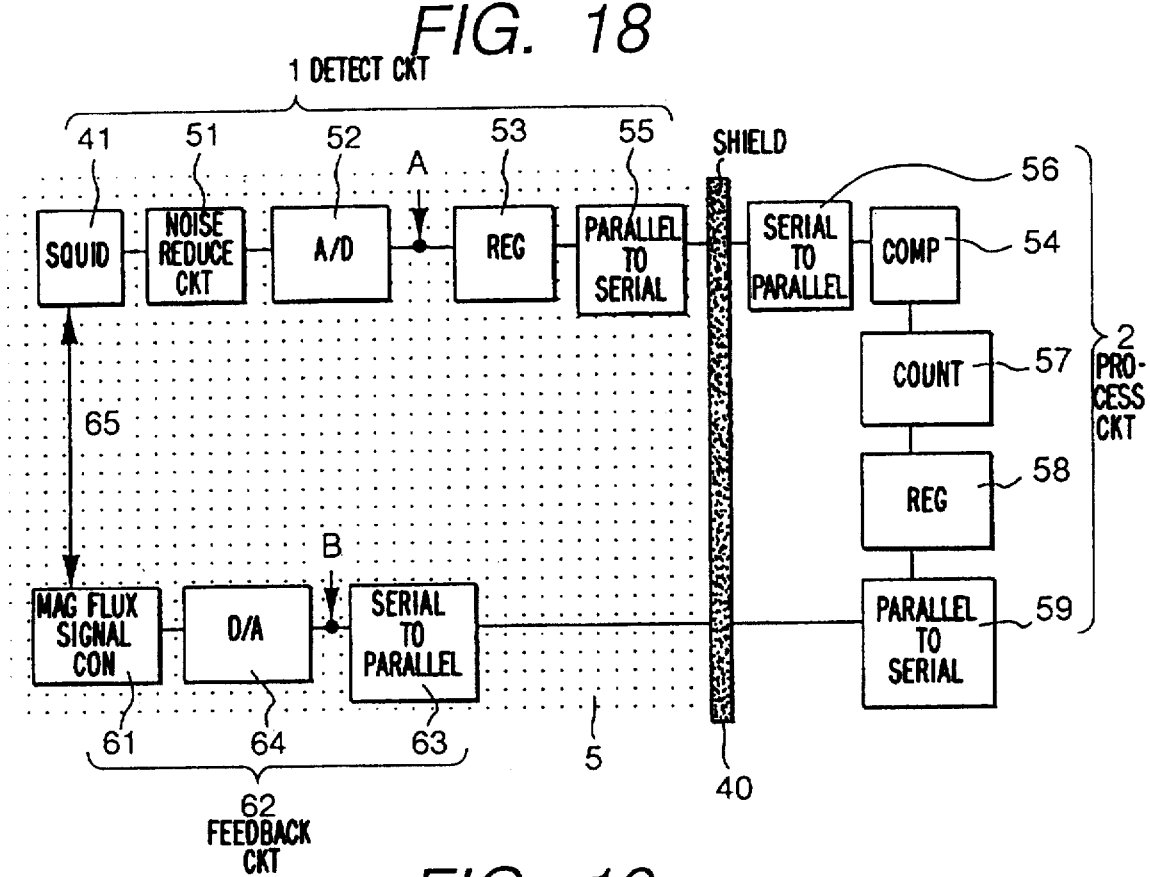
FIG. 18 is a block diagram illustrating one configuration of the measurement system for measuring material deterioration in a ninth embodiment using the digital SQUID.

The following describes a further embodiment according to the invention with reference to FIG. 18. The configuration of the measurement system for material deterioration according to the present embodiment is as shown in FIG. 15, the difference from the configuration in FIG. 15 being that comparator 54 is located in the signal processing circuit 2. In the embodiment given in FIG. 15, the comparator 54 is contained in the detection circuit 1, so it was sufficient that only the result of comparing the output sent from the SQUID 41 with the value in the comparator 54 is transmitted to the signal processing circuit 2. In the present embodiment, by contrast, the result of converting the output signal from the SQUID 41 into digital value is sent to the signal processing circuit 2; then it is compared with a value in the comparator. This will result in increased amount of the signal to be sent from the detection circuit 1 comprising the superconductive device to the signal processing circuit 2 comprising the semiconductor device. However, the number of circuits comprising the superconductors is smaller than that in the embodiment shown in FIG. 15; this facilitates manufacturing.

It is apparent, furthermore, that the same effects can be gained when the noise eliminating means 51 placed between the SQUID 41 and the analog to digital converter 52 in FIG. 18 is installed at a position between the analog to digital converter 52 and the register 53, as indicated by point A in FIG. 18. It is also possible to install the noise eliminating means 51 shown in FIG. 19 between the serial to parallel converter 56 of the signal processing circuit 2 and the comparator 54.

Figure 19:
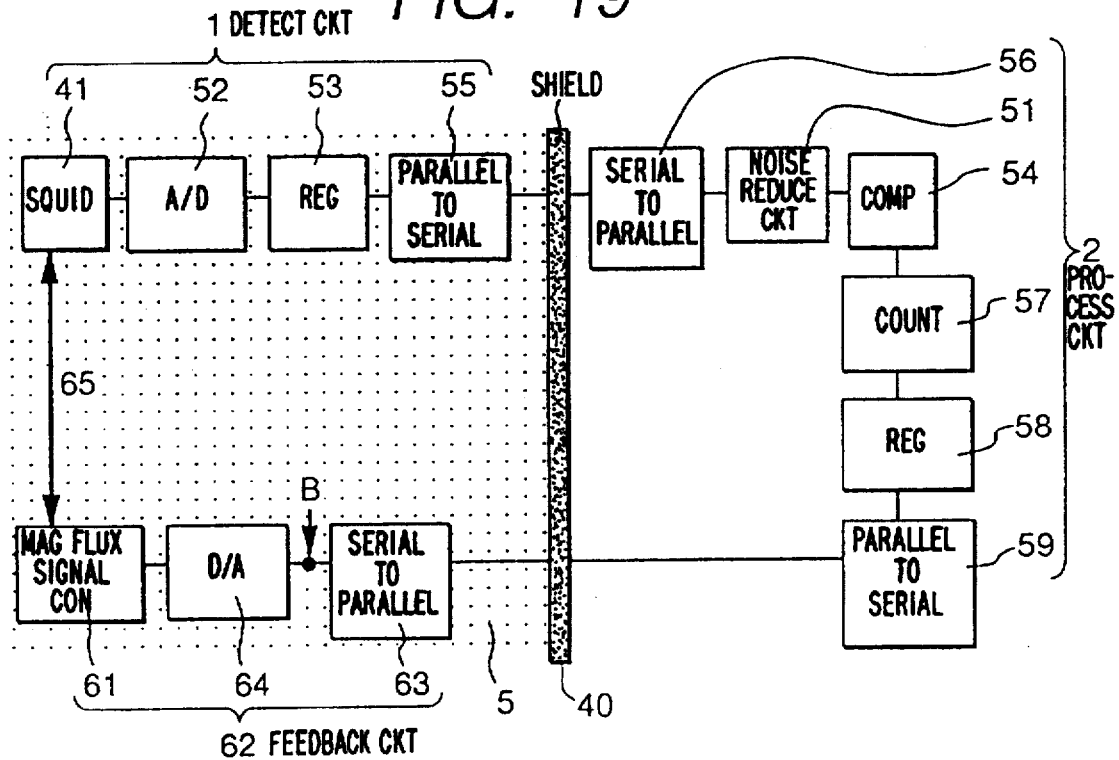
FIG. 19 is a block diagram illustrating another configuration of the measurement system for measuring material deterioration in the ninth embodiment using the digital SQUID.

The register 58 installed at the signal processing circuit 2 in FIGS. 18 and 19 can be installed inside the feedback circuit 62 indicated by points B in FIGS. 18 and 19. It is apparent that, even when the circuit of the measurement system for material deterioration is configured as in the present embodiment, the present embodiment provides a measurement system for material deterioration featuring a long time use inside the nuclear reactor with high accuracy and a stable operation, similar to the case of the embodiment shown in FIG. 15.

Tenth Embodiment

Figure 20:
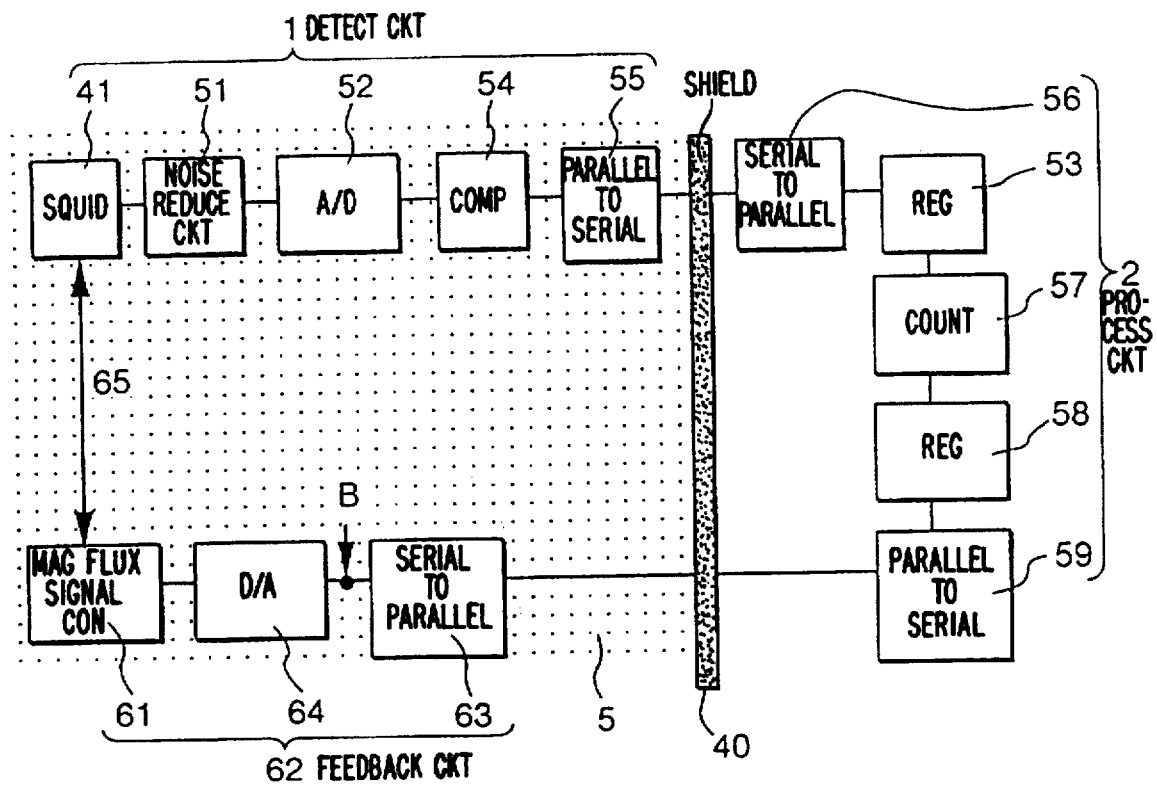
FIG. 20 is a block diagram illustrating one configuration of the measurement system for measuring material deterioration in a tenth embodiment using the digital SQUID.

The following describes a still further embodiment according to the invention with reference to FIG. 20. The configuration of the measurement system for material deterioration according to the present embodiment is as shown in FIG. 15, the difference from the configuration in FIG. 15 being that the register 53 located at the detection circuit 1 in FIG. 15 is installed in the signal processing circuit 2 in the present embodiment. When the operation speed of the comparator 54 is sufficiently higher than that of the analog to digital converter 52, it is possible to use the circuit configuration in the present embodiment. According to the circuit configuration shown in the present embodiment, the number of the components of the detection circuit 1 is reduced below that in the circuit in the embodiment given in FIG. 15, giving an advantage of providing easier production.

The register 58 installed in the signal processing circuit 2 can be installed in the feedback circuit 62 as indicated by point B in FIG. 20.

It is apparent that the present configuration provides the same effects as those of the circuit in the embodiment of FIG. 15.

Eleventh Embodiment

Figure 21:
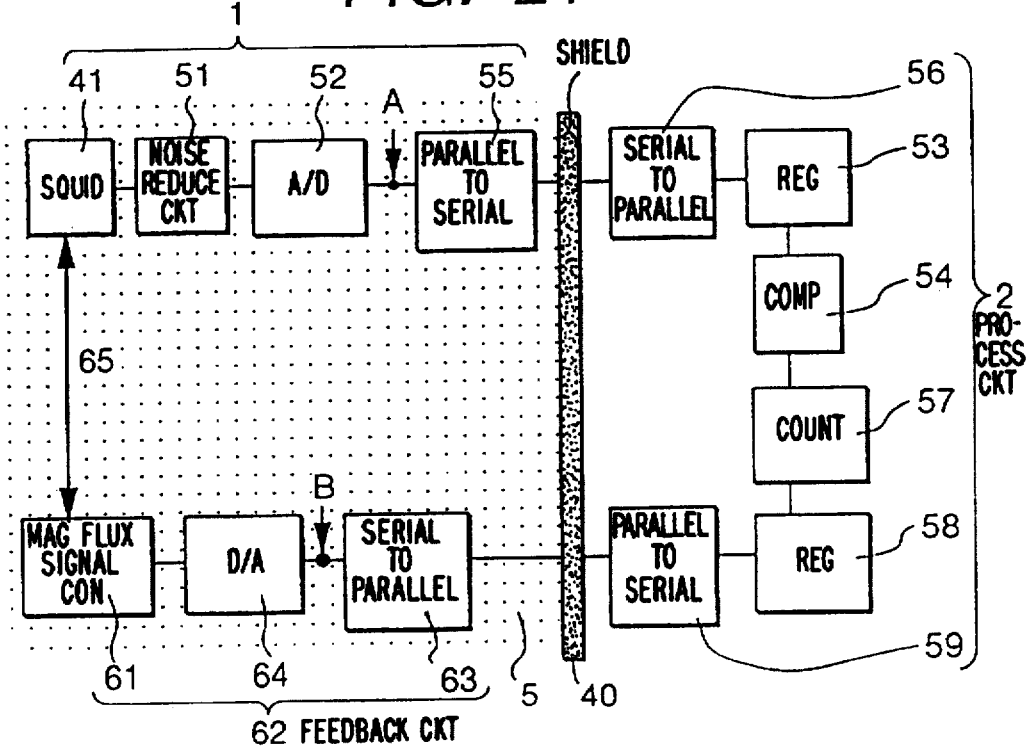
FIG. 21 is a block diagram illustrating one configuration of the measurement system for material deterioration in an eleventh embodiment using the digital SQUID.

The following describes another embodiment according to the invention with reference to FIG. 21. The detection circuit 1 in FIG. 21 comprises a SQUID 41, a noise eliminating means 51 to eliminate noise having occurred to the SQUID due to gamma ray, an analog to digital converter 52 to convert into a plurality of bits of the parallel digital signals the analog signals issued from the SQUID 41, and a parallel to serial converter 55 to convert into the serial signals the parallel signals sent from the analog to digital converter 52. The differences between the present embodiment and that in FIG. 15 are that the register 53 and the comparator 54 are installed in the signal processing circuit 2 in the case of the present embodiment. In the configuration given in FIG. 21, there is an increased amount of the signal to be sent from the detection circuit 1 to the signal processing circuit 2 over that in the embodiment shown in FIG. 15. However, the number of the components of the detection circuit 1, namely, the number of circuits comprising the superconductive devices, is smaller; this facilitates manufacturing.

In FIG. 21, furthermore, it is apparent that the same effects can be gained when the noise eliminating means 51 installed between the SQUID 41 and the analog to digital converter 52 is installed between the analog to digital converter 52 and the parallel to serial converter 55 as shown by the point A in FIG. 21. Furthermore, the noise eliminating means 51 can be installed between the serial to parallel converter 56 of the signal processing circuit 2 and the register 53, as shown in FIG. 22.

Figure 22:
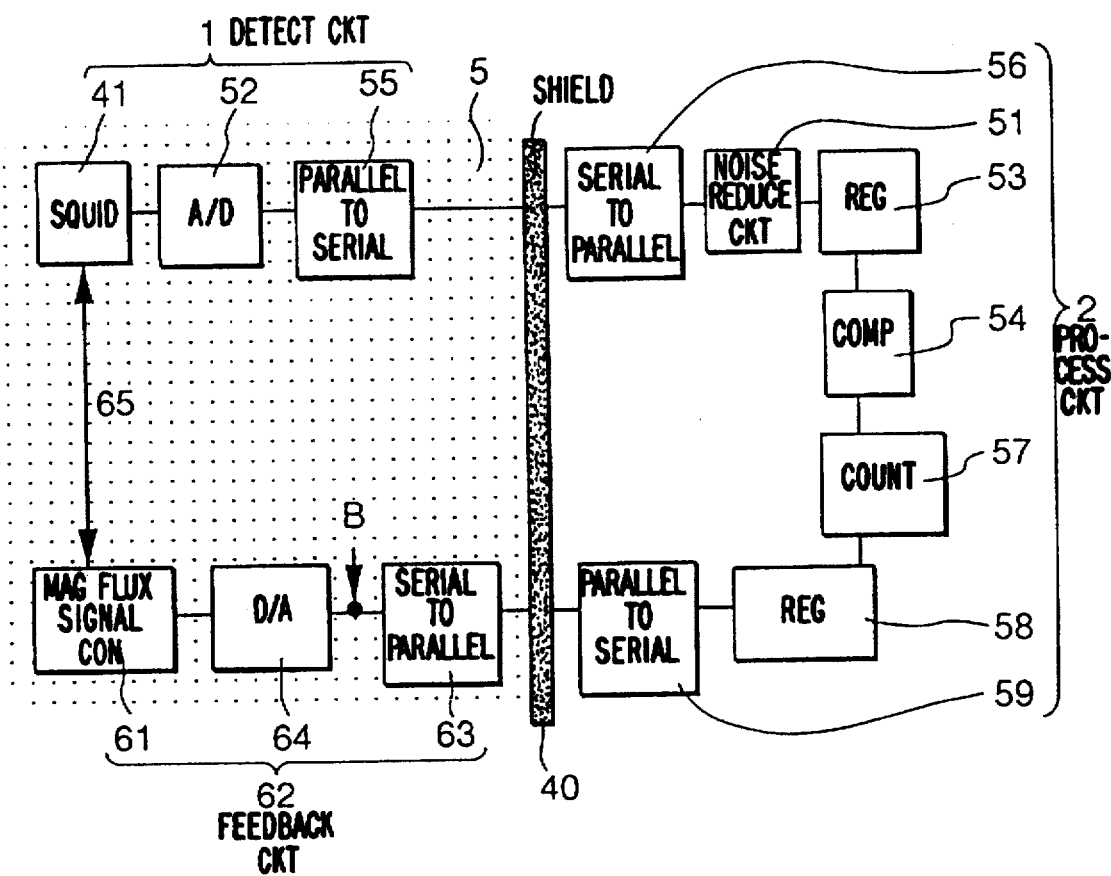
FIG. 22 is a block diagram illustrating another configuration of the measurement system for measuring material deterioration in the eleventh embodiment using the digital SQUID.
Figure 23:
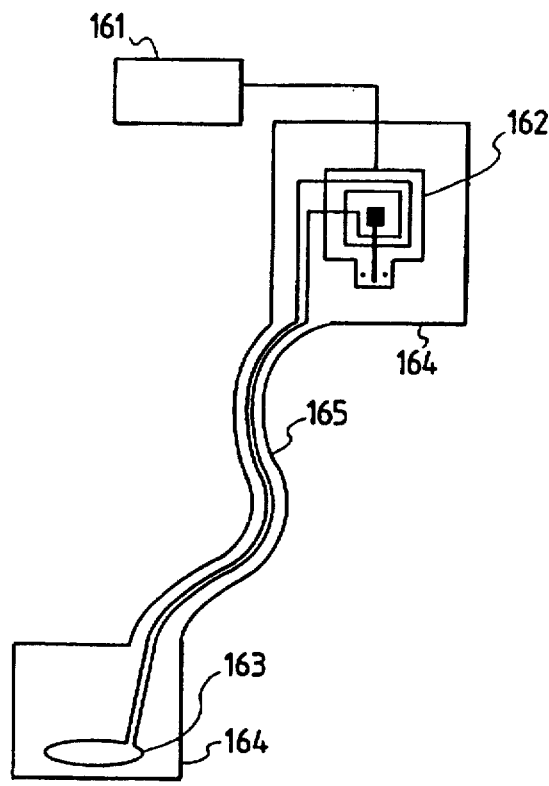
FIG. 23 is a diagram illustrating the configuration of a conventional measurement system for material deterioration using the analog SQUID.
Figure 24:
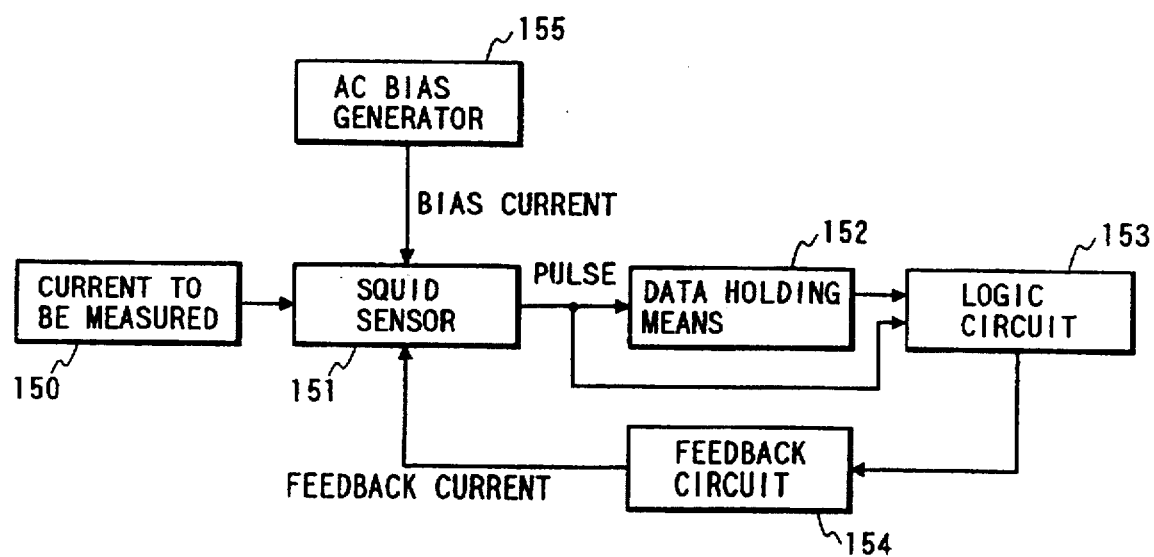
FIG. 24 is a diagram illustrating a conventional measurement system for material deterioration using the analog SQUID.

In FIGS. 21 and 22, the register 58 installed in the signal processing circuit 2 can be installed in the feedback circuit 62, as indicated by the points B in FIGS. 21 and 22. It is apparent that, even when the circuit of the measurement system for material deterioration is configured as in the present embodiment, the present embodiment provides a measurement system for material deterioration featuring a long time use inside the nuclear reactor with high accuracy and a stable operation, similar to the case of the embodiment shown in FIG. 15.

Some of said embodiments do not specify the material of the superconductor constituting the detection circuit. It is apparent that the same effects can be gained when any one of the metal low-temperature superconductor, the oxide high-temperature superconductor and a combination of the two is used to form the detection circuit. Furthermore, when only the high-temperature superconductor is used to form the detection circuit, liquid nitrogen can be used as cryogen to cool the superconductor. It is apparent that this ensures easier handling of the measurement system for measuring material deterioration, leading to a cost reduction.

What is claimed is:

1. A measurement system for measuring material deterioration in accordance with a magnetic field of the material in the presence of gamma ray radiation, the measurement system at least including:

(a) a detection circuit which detects the magnetic field of the material and generates a signal indicative thereof, said detection circuit including a magnetic flux sensor using superconductors;

(b) a signal processing circuit at least including semiconductor devices to process the signal generated from said detection circuit; and (c) a noise reducing circuit which at least reduces noise in the generated signal due to the gamma ray radiation;

wherein said signal processing circuit is installed at a place where a dose equivalent of radiation is equal to or smaller than that of a place where said detection circuit is installed.

2. A measurement system for measuring material deterioration according to claim 1 wherein said magnetic flux sensor is composed of the high-temperature superconductor.

3. A measurement system for measuring material deterioration according to claim 1 wherein a substance to dampen radiation intensity is located between said detection circuit and signal processing circuit.

4. A measurement system for measuring material deterioration according to claim 1 wherein said signal processing circuit is installed outside a nuclear reactor pressure receptacle.

5. A measurement system for measuring material deterioration according to claim 4 wherein said pressure receptacle contains water.

6. A measurement system for measuring material deterioration according to claim 5 wherein said signal processing circuit is installed inside said pressure receptacle.

7. A measurement system for measuring material deterioration according to claim 6 wherein said signal processing circuit is installed on the bottom of said pressure receptacle.

8. A measurement system for measuring material deterioration according to claim 6 wherein said signal processing circuit is installed outside a shroud located inside said pressure receptacle.

9. A measurement system for measuring material deterioration according to claim 6 wherein said signal processing circuit is installed close to the top of said pressure receptacle.

10. A measurement system for measuring material deterioration according to claim 1 wherein said signal processing circuit is installed where radiation dose equivalent is equal to or smaller than $10^2$ rems.

11. A measurement system for measuring material deterioration according to claim 1 wherein at least said signal processing circuit is installed in a low temperature vessel.

12. A measurement system for measuring material deterioration using a digital signal according to claim 11 wherein said detection circuit is installed at the temperature of liquid helium or liquid nitrogen.

13. A measurement system for measuring material deterioration according to claim 11 wherein at least said low temperature vessel has a means for waterproofing to ensure its use under water.

14. A measurement system for measuring material deterioration according to claim 11 wherein at least said low temperature vessel has a means for resisting pressure to ensure its use under water.

15. A measurement system for measuring material deterioration according to claim 1 wherein said signal transmitting means has a means for waterproofing and means for resisting pressure to ensure its use under water.

16. A measurement system for measuring material deterioration according to claim 5 wherein the portion of said measurement system installed under water has a sufficient weight to keep its position under water.

17. A measurement system for measuring material deterioration according to claim 11 wherein said low temperature vessel has a cryogen supply means and a means to ensure a constant pressure inside said low temperature vessel.

18. A measurement system for measuring material deterioration according to claim 17 wherein said cryogen supply means and said means to ensure a constant pressure inside low temperature vessel is a pipe connecting between said low temperature vessel and the outside of the pressure receptacle.

19. A measurement system for measuring material deterioration according to claim 1 wherein said signal transmission means among circuits is based on optical transmission and optical modulation system, and the light emitter and light receiver are installed where radiation dose equivalent is equal to or smaller than that at the position of said signal processing circuit.

20. A measurement system for measuring material deterioration according to claim 1 further comprising signal transmission means based on an optical transmission and optical modulation system for enabling transmission of the generated signal between said detection circuit and said signal processing circuit, and a light emitter and light receiver are installed where radiation dose equivalent is equal to or smaller than $10^2$ rems.

21. A measurement system for measuring material deterioration according to claim 1 wherein said magnetic flux sensor contained in said detection circuit is a SQUID including at least one Josephson junction device.

22. A measurement system for measuring material deterioration according to claim 21 wherein said SQUID has a signal input coil and signal detecting coil.

23. A measurement system for measuring material deterioration according to claim 22 wherein said signal input coil is made contact with signal detecting coil by using screws or springs to hold down the end of a superconductor wire forming said signal detecting coil or a normal conducting wire, and the end of the superconductor wire forming said signal input coil.

24. A measurement system for measuring material deterioration according to claim 22 wherein said magnetic flux sensor contained in said detection circuit has a signal input coil and signal detecting coil, and said signal detecting coil and said signal input coil are formed on the same substrate as that of said magnetic flux sensor.

25. A measurement system for measuring material deterioration according to claim 1 wherein said noise reducing circuit is a filter comprising capacitors and resistors.

26. A measurement system for measuring material deterioration according to claim 1 further comprising a shield using a superconductor to reduce or eliminate environmental noise.

27. A measurement system for measuring material deterioration according to claim 1 further comprising guard rings or moats installed around said magnetic flux sensor to reduce or eliminate environmental noise.

28. A measurement system for measuring material deterioration according to claim 1 wherein said noise reducing circuit offsets the noise by differential detection of signals from two SQUIDs.

29. A measurement system for measuring material deterioration according to claim 1 comprising a means to detect spatial position at the measuring site.

30. A measurement system for measuring material deterioration according to claim 1 comprising a means to ensure a constant distance between the measuring site and measured object.

31. A measurement system for measuring material deterioration according to claim 29 wherein said position detecting means or said means to ensure a constant distance between the measuring site and measured object is a probing method.

32. A measurement system for measuring material deterioration according to claim 29 wherein said position detecting means is a means using a camera.

33. A measurement system for measuring material deterioration according to claim 29 wherein said position detecting means and said means to ensure a constant distance use sound waves.

34. A measurement for measuring material deterioration according to claim 1 wherein said detection circuit provides a digital signal output.

35. A measurement system for measuring material deterioration according to claim 1 wherein said detection circuit has a amplifier using superconductor to amplify the output from said magnetic flux sensor.

36. A measurement system for measuring material deterioration according to claim 1 wherein at least said detection circuit has a means for waterproofing and means for resisting pressure to ensure its use under water.

37. A measurement system for measuring material deterioration according to claim 1 wherein at least said signal processing circuit has a means for waterproofing and means for resisting pressure to ensure its use under water.

38. A measurement for measuring material deterioration according to claim 1 further comprising signal transmitting means for enabling transmission of the generated signal between said detection circuit and said signal processing signal, at least said signal transmitting means has a means for waterproofing and means for resisting pressure to ensure its use under water.

39. A measurement system for measuring material deterioration according to claim 1 wherein said detection circuit has a feedback circuit for transmitting a feedback signal from said signal processing circuit to said magnetic flux sensor contained in said detection circuit.

40. A measurement system for measuring material deterioration according to claim 39 wherein said feedback circuit has at least a portion which is manufactured with a superconductor, and said portion manufactured with the superconductor is installed inside a low temperature vessel which contains said detection circuit.

41. A measurement for measuring material deterioration according to claim 39 wherein said detection circuit at least comprises:
(1) a SQUID comprising at least one Josephson junction device;
(2) a means to convert into a plurality of bits of parallel digital signals analog signals such as output voltage and output current issued from said SQUID; and
(3) a parallel to serial converter to convert said parallel digital signals into said serial digital signals;

said signal processing circuit at least comprises:
(1) a first serial/parallel converter to convert the said serial digital signal into the parallel digital signal;
(2) a counter; and
(3) a second parallel/serial converter to convert into the serial digital signal the parallel digital signal sent from said counter;

said feedback circuit at least comprises:
(1) a second serial/parallel converter to convert into the parallel digital signal said serial digital signal sent from said signal processing circuit;
(2) a means to convert the digital signal into the analog signal; and
(3) a means to convert into the magnetic flux signal the signal sent from said means for converting the digital signal into the analog signal;

wherein
(1) at least either said detection circuit or said signal processing circuit has a first register,
(2) at least either said detection circuit or said signal processing circuit has a second register, and
(3) at least either said detection circuit or signal processing circuit includes said noise reducing circuit.

42. A measurement system for measuring material deterioration according to claim 41 wherein said reducing noise circuit is a filter comprising capacitors and resistors installed in said detection circuit.

43. A measurement system for measuring material deterioration according to claim 41 wherein said reducing noise circuit is a filter comprising a capacitor and resistor installed in said signal processing circuit.

44. A measurement system for measuring material deterioration according to claim 41 wherein said reducing noise circuit is a digital filter in said detection circuit.

45. A measurement system for measuring material deterioration according to claim 41 wherein said reducing noise circuit is a digital filter in said signal processing circuit.

46. A measurement system for measuring material deterioration according to claim 41 wherein a magnetic flux signal generated by a means to convert into the magnetic flux signal a signal sent from said means to convert a digital signal to an analog signal is subjected to magnetic coupling with said magnetic flux sensor.

47. A measurement system for measuring material deterioration according to claim 41 wherein said means to convert the digital signal to the analog signal is a digital to analog converter, and said means to convert into the magnetic flux signal said signal sent from said digital to analog converter is composed of resistors and inductances.

48. A measurement system for measuring material deterioration according to claim 1 wherein
said detecting circuit, said signal processing circuit and a signal transmitting means for enabling transmission of the generated signal between said detection circuit and said signal processing circuit and constituting said measurement system comprise at least one part or a combination of a plurality of parts; and at least one part, at least one combination of a plurality of said parts, at least said circuit or said signal transmitting means are provided with standby parts.

49. A measurement system for measuring material deterioration according to claim 1 wherein
materials at a plurality of places can be measured simultaneously.

50. A measurement system for measuring material deterioration according to claim 49 wherein a plurality of places includes at least three intersecting positions.

51. A measurement system for measuring material deterioration in accordance with a magnetic field of the material in the presence of gamma ray radiation, the measurement system at least comprising:
(1) a first circuit having great enduring power to gamma ray radiation; and
(2) a second circuit having weaker enduring power to gamma ray radiation than said first circuit;
wherein said first circuit is used for measuring the magnetic field of the material and generating signals indicative thereof and having noise due to the gamma ray radiation, and said second circuit is used for processing signals from said first circuit which are reduced in noise at least due to gamma ray radiation by a third circuit.

52. A measurement system for measuring material deterioration according to claim 51, wherein a substance to dampen radiation intensity is located between said first circuit and said second circuit.

53. A measurement system for measuring material deterioration according to claim 1 wherein the magnetic flux sensor of the detection circuit is configured without a radiation shield.

54. A measurement system for measuring material deterioration according to claim 51, wherein the first circuit includes a magnetic flux sensor configured without a radiation shield.

* * * * *